United States Patent
Nakao et al.

(10) Patent No.: US 11,638,730 B2
(45) Date of Patent: May 2, 2023

(54) CANCER THERAPY BY COMBINATION USE OF ONCOLYTIC VACCINIA VIRUS AND IMMUNE CHECKPOINT INHIBITOR, AND PHARMACEUTICAL COMPOSITION AND COMBINATION MEDICINE FOR USE IN THE CANCER THERAPY

(71) Applicant: ASTELLAS PHARMA INC., Tokyo (JP)

(72) Inventors: Shinsuke Nakao, Tokyo (JP); Tatsuya Kawase, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 17/279,937

(22) PCT Filed: Sep. 25, 2019

(86) PCT No.: PCT/JP2019/037448
§ 371 (c)(1),
(2) Date: Mar. 25, 2021

(87) PCT Pub. No.: WO2020/067085
PCT Pub. Date: Apr. 2, 2020

(65) Prior Publication Data
US 2021/0315951 A1 Oct. 14, 2021

(30) Foreign Application Priority Data
Sep. 26, 2018 (JP) .............................. JP2018-179632

(51) Int. Cl.
*A61K 35/768* (2015.01)
*A61K 38/20* (2006.01)
*A61K 48/00* (2006.01)
*A61P 35/00* (2006.01)
*A61P 35/04* (2006.01)
*C12N 15/24* (2006.01)
*A61K 39/395* (2006.01)
*C12N 7/00* (2006.01)
*A61K 39/00* (2006.01)

(52) U.S. Cl.
CPC .......... *A61K 35/768* (2013.01); *A61K 38/208* (2013.01); *A61K 38/2046* (2013.01); *A61K 39/39558* (2013.01); *A61P 35/00* (2018.01); *A61P 35/04* (2018.01); *C12N 7/00* (2013.01); *A61K 2039/545* (2013.01); *C12N 2710/24132* (2013.01); *C12N 2710/24143* (2013.01)

(58) Field of Classification Search
None
See application file for complete search history.

(56) References Cited

U.S. PATENT DOCUMENTS

| | | | |
|---|---|---|---|
| 6,379,674 | B1 | 4/2002 | Rabkin et al. |
| 9,809,803 | B2 | 11/2017 | Nakamura |
| 2002/0018767 | A1 | 2/2002 | Lee et al. |
| 2006/0099224 | A1 | 5/2006 | Kirn |
| 2007/0077231 | A1 | 4/2007 | Contag et al. |
| 2007/0264235 | A1 | 11/2007 | Erbs |
| 2007/0298054 | A1 | 12/2007 | Shida et al. |
| 2009/0053244 | A1 | 2/2009 | Chen et al. |
| 2010/0297072 | A1 | 11/2010 | Depinho |
| 2013/0071430 | A1 | 3/2013 | Nakamura et al. |
| 2013/0195800 | A1 | 8/2013 | Roeth et al. |
| 2013/0302367 | A1 | 11/2013 | Shida et al. |
| 2015/0004188 | A1 | 1/2015 | Weiner et al. |
| 2016/0129135 | A1 | 5/2016 | Kirn |
| 2016/0281066 | A1 | 9/2016 | Nakamura |
| 2017/0340687 | A1 | 11/2017 | Nakao et al. |
| 2018/0185515 | A1 | 7/2018 | Hicklin et al. |
| 2020/0289592 | A1 | 9/2020 | Nakamura et al. |
| 2020/0338149 | A1 | 10/2020 | Nakao et al. |

FOREIGN PATENT DOCUMENTS

| | | |
|---|---|---|
| CA | 2387855 A1 | 4/2001 |
| CA | 2931294 A1 | 5/2015 |
| EP | 3 480 307 A1 | 5/2019 |
| JP | 2001-513508 A | 9/2001 |
| JP | 2003-512335 A1 | 4/2003 |
| JP | 2006-506974 A | 3/2006 |
| JP | 2012-527465 A | 11/2012 |
| JP | 2013-527753 A | 7/2013 |
| WO | WO-01/28583 A2 | 4/2001 |
| WO | WO-2005/054451 A1 | 6/2005 |
| WO | WO-2007/038276 A2 | 4/2007 |

(Continued)

OTHER PUBLICATIONS

Genetically Engineered Vaccinia Virus, 2017, translation of WO 2017209053, pp. 1-46.*
Liu et al., The Targeted Oncolytic Poxvirus JX-594 Demonstrates Antitumoral, Antivascular, and Anti-HBV Activities in Patients With Hepatocellular Carcinoma, Molecular Therapy, vol. 16, No. 9, The American Society of Gene Therapy, Sep. 2008, pp. 1637-1642.
Thorne et al., Rational Strain Selection and Engineering Creates a Broad-Spectrum, Systemically Effective Oncolytic Poxvirus, JX-963, The Journal of Clinical Investigation, vol. 117, No. 11, Nov. 2007, pp. 3350-3358.
Chalikonda et al., "Oncolytic virotherapy for ovarian carcinomatosis using a replication-selective vaccinia virus armed with a yeast cytosine deaminase gene," Cancer Gene Ther., Feb. 2008 (Epub Dec. 14, 2007), 15(2):115-125.

(Continued)

*Primary Examiner* — Maria Marvich
(74) *Attorney, Agent, or Firm* — Foley & Lardner LLP

(57) ABSTRACT

The present invention provides a combination therapy of genetically modified vaccinia virus (particularly oncolytic vaccinia virus) and another cancer therapy for use in treating cancer, and a pharmaceutical composition and a combination kit for use in the therapy. More specifically, the invention provides a therapy with vaccinia virus containing a polynucleotide encoding interleukin-7 (IL-7) and a polynucleotide encoding interleukin-12 (IL-12) in combination with an immune checkpoint inhibitor, and a pharmaceutical composition and a combination kit for use in the therapy.

8 Claims, 1 Drawing Sheet

(56) References Cited

FOREIGN PATENT DOCUMENTS

| WO | WO-2008/134879 A1 | 11/2008 | | |
|---|---|---|---|---|
| WO | WO-2011/119773 A1 | 9/2011 | | |
| WO | WO-2011/125469 A1 | 10/2011 | | |
| WO | WO-2012/151272 A2 | 11/2012 | | |
| WO | WO-2015/076422 A1 | 5/2015 | | |
| WO | WO-2015/124297 A1 | 8/2015 | | |
| WO | WO-2015/150809 A1 | 10/2015 | | |
| WO | WO-2016/205429 A1 | 12/2016 | | |
| WO | WO-2017/079746 A2 | 5/2017 | | |
| WO | WO-2017/118866 A1 | 7/2017 | | |
| WO | WO-2017/147554 A2 | 8/2017 | | |
| WO | WO-2017/209053 A1 | 12/2017 | | |
| WO | WO-2018/057943 A1 | 3/2018 | | |
| WO | WO-2018111902 A1 | * | 6/2018 | ............ A61K 38/162 |
| WO | WO-2018195552 A1 | * | 10/2018 | .............. A61P 35/00 |

OTHER PUBLICATIONS

Chen et al., "Elements of cancer immunity and the cancer-immune set point," Nature, Jan. 19, 2017, 541:321-330.

Chen et al., "Low-Dose Vaccinia Virus-Mediated Cytokine Gene Therapy of Glioma," Journal of Immunotherapy, 2001, 24(1):46-57.

Fumoto et al., Targeted Gene Delivery: Importance of Administration Routes, Novel Gene Therapy Approaches, 2013, Chapter 1, 1-30.

Guse et al., "Oncolytic vaccinia virus for the treatment of cancer," Expert Opin. Biol. Ther., Feb. 22, 2011, 11(5):595-608.

Hikichi et al., "MicroRNA Regulation of Glycoprotein B5R in Oncolytic Vaccinia Virus Reduces Viral Pathogenicity Without Impairing Its Antitumor Efficacy," Molecular Therapy, Jun. 2011, 19(6):1107-1115.

Hill et al., "Achieving systemic delivery of oncolytic viruses," Expert Opinion on Drug Delivery, May 30, 2019, 1-15.

Leong et al., "Interleukin-7 Enhances Cell-Mediated Immune Responses In vivo in an Interleukin-2-Dependent Manner," Viral Immunology, 1997, 10(1):1-9.

Mehrotra et al., "Synergistic Effects of IL-7 and IL-12 on Human T Cell Activation," The Journal of Immunology, May 1, 1995, 154:5093-5102.

Ortiz-Sanchez et al., "Antibody-cytokine fusion proteins: applications in cancer therapy," Expert Opin. Biol. Ther., May 2008, 8(5):609-632.

Postow et al., "Immune-Related Adverse Events Associated with Immune Checkpoint Blockade," N. Eng. J. Med., Jan. 11, 2018, 378(2):158-168.

Schilbach et al., "Cancer-targeted IL-12 controls human rhabdomyosarcoma by senescence induction and myogenic differentiation," OncoImmunology, Jul. 2015, 4(7):e1014760, 1-14.

Shen et al., "Fighting Cancer with Vaccinia Virus: Teaching New Tricks to an Old Dog," Molecular Therapy, Feb. 2005, 11(2):180-195.

Shida et al., "Effects and Virulences of Recombinant Vaccinia Viruses Derived from Attenuated Strains That Express the Human T-Cell Leukemia Virus Type I Envelope Gene," Journal of Virology, Dec. 1988, 62(12):4474-4480.

Weiss et al., "Immunotherapy of cancer by IL-12-based cytokine combinations," Expert Opin. Biol. Ther., Nov. 1, 2007, 7(11):1705-1721.

Yakubitskyi et al., "Highly Immunogenic Variant of Attenuated Vaccinia Virus," Biochemistry, Biophysics and Molecular Biology, 2016, 466(2):241-244, with English translation.

Yakubitskyi et al., "Highly Immunogenic Variant of Attenuated Vaccinia Virus," Biochemistry, Biophysics and Molecular Biology, 2016, 466:35-38.

Zheng et al., "Oncolytic Viruses for Cancer Therapy: Barriers and Recent Advances," Molecular Therapy: Oncolytics, Dec. 15, 2019, 15:234-247.

Bell et al., Antibodies against the extracellular enveloped virus B5R protein are mainly responsible for the EEV neutralizing capacity w of vaccinia immune globulin, 2004 Virology, pp. 425-431.

Kurosaki et al., Anti-Tumor Effects of MAPK-Dependent Tumor-Selective Oncolytic Vaccinia Virus Armed with CD/UPRT against V Pancreatic Ductal Adenocarcinoma in Mice, Cells 2021, pp. 1-17.

Rodger et al., "Replacing the SCR domains of vaccinia virus protein B5R with EGFP causes a reduction in plaque size and actin tail formation but enveloped virions are still transported to the cell surface," Journal of General Virology, 2002, 83:323-332.

Tang et al., "A cautionary note on the selectivity of oncolytic poxviruses," Oncolytic Virotherapy, 2019, 8:3-8.

Jorgensen et al., "Recent trends in stabilising peptides and proteins in pharmaceutical formulation—considerations in the choice of excipients," Expert Opin. Drug Deliv., 2009, 6(11):1219-1230.

Mashkovsky, M.D., Medicines, 16th Edition, 2012, pp. 12-13 with English translation.

McCloskey et al., "Ovarian Cancer Immunotherapy: Preclinical Models and Emerging Therapeutics," Cancers, Jul. 26, 2018, 10(8):244, 1-30.

Tyagi et al., "Use of Chemical Modification and Chemical Cross-Linking for Protein Stabilization (Enzymes)," Biochemistry, 1998, 63(3):395-407, with English abstract.

Jakubke et al., Amino Acids, Peptides and Proteins, "Mir," Moscow, 1985, 92-94, with English translation.

Herrera et al., "Functional Analysis of Vaccinia Virus B5R Protein: Essential Role in Virus Envelopment is Independent of a Large Portion of the Extracellular Domain," Journal of Virology, Jan. 1988, 72(1):294-302.

Mathew et al., "The Extracellular Domain of Vaccinia Virus Protein B5R Affects Plaque Phenotype, Extracellular Enveloped Virus Release, and Intracellular Actin Tail Formation," Journal of Virology, Mar. 1998, 72(3):2429-2438.

* cited by examiner

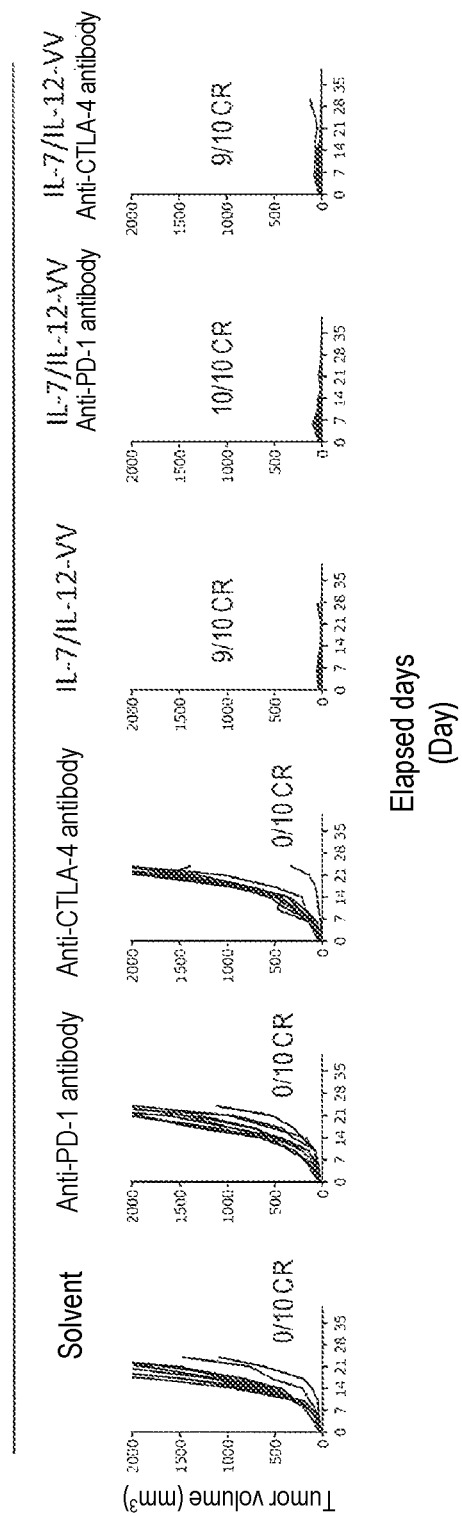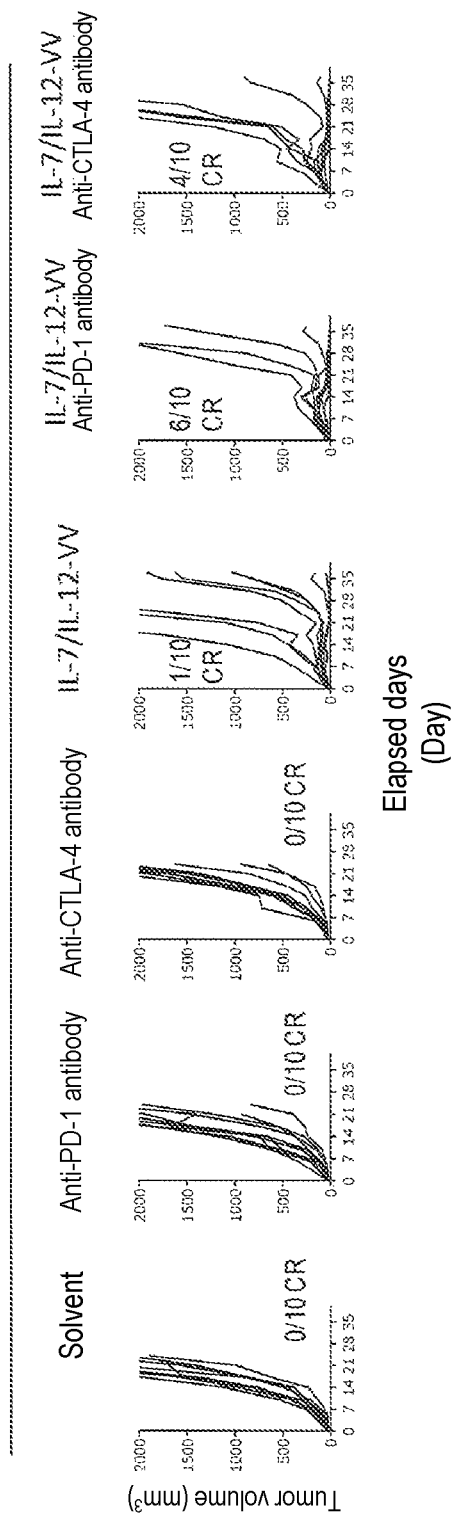

CANCER THERAPY BY COMBINATION USE OF ONCOLYTIC VACCINIA VIRUS AND IMMUNE CHECKPOINT INHIBITOR, AND PHARMACEUTICAL COMPOSITION AND COMBINATION MEDICINE FOR USE IN THE CANCER THERAPY

CROSS-REFERENCE TO RELATED APPLICATIONS

This application is the U.S. National Stage of PCT/JP2019/037448, filed Sep. 25, 2019, which claims priority to JP 2018-179632, filed Sep. 26, 2018.

BACKGROUND OF THE INVENTION

Field of the Invention

The present invention relates to a cancer therapy by combination use of an oncolytic vaccinia virus and an immune checkpoint inhibitor, and a pharmaceutical composition and a combined medicine for use in the cancer therapy.

Description of Related Art

Recently, various technologies have been developed for using viruses in cancer therapy. Vaccinia virus is known as a virus for use in cancer therapy. Vaccinia virus has been investigated for the purpose of developing a cancer therapy, as an oncolytic virus proliferating in cancer cells to destroy them, as a vector for delivering a therapeutic gene to cancer cells or as a cancer vaccine expressing a cancer antigen and an immune regulatory molecule (Expert Opinion on Biological Therapy, 2011, Vol. 11, p. 595-608).

It is reported that genetically modified vaccinia virus containing two polynucleotides, i.e., a polynucleotide encoding interleukin-7 (IL-7) and a polynucleotide encoding interleukin-12 (IL-12), and a mixture of two genetically modified vaccinia viruses, i.e., a genetically modified vaccinia virus containing a polynucleotide encoding IL-7 and a genetically modified vaccinia virus containing a polynucleotide encoding IL-12, have cytolytic action on various types of human cancer cells, tumor regression action in a tumor-bearing humanized mouse model, complete remission in a syngenic tumor-bearing mouse model, and further induce acquired immunity to maintain an antitumor effect (Patent Document 1).

On the other hand, in recent years, a cancer immunotherapy based on the mechanism of anti-tumor immune control in the microenvironment of cancer have been clinically studied. For the purpose of activating the in vivo immune mechanism by inhibiting the binding between PD-1 (programmed cell death-1) and PD-L1 (programmed cell death-1 ligand-1) to allow the living body to recognize cancer cells as non-self cells, thereby eliminating cancer cells, an anti-PD-1 antibody such as nivolumab and pembrolizumab, and an anti-PD-L1 antibody such as atezolizumab, avelumab and durvalumab have been approved as therapeutic agents for cancer by the U.S. Food And Drug Administration (FDA) (Non Patent Document 1). Similarly, for the purpose of activating a mechanism to eliminate cancer cells as non-self cells by the in-vivo immune system, anti-CTLA-4 (cytotoxic T-lymphocyte associated antigen 4) antibody, i.e., ipilimumab, has been approved as a therapeutic agent for cancer (Non Patent Document 1). Cancer immunotherapeutic agents containing these immune checkpoint inhibitors are not only used singly but also in combination with an existing anti-cancer agent or another type of cancer immunotherapeutic agent (Non Patent Document 2). It is reported that oncolytic vaccinia virus expressing an immunostimulatory molecule may have a possibility of promptly being cleared by strong immune response of the immune checkpoint inhibitor. The strong immune response can be a foe in some cases and a friend in other cases for vaccinia virus-mediated cancer therapy (Non Patent Document 3).

PRIOR ART DOCUMENTS

Patent Document

Patent Document 1: WO 2017/209053 pamphlet
Non Patent Document 1: Michael A. Postow et al., The New England Journal of Medicine, 2018, Vol. 378, p. 158-168
Non Patent Document 2: Daniel S. Chen and Ira Mellman, Nature, 2017, Vol. 541, p. 321-330
Non Patent Document 3: Yuqiao Shen and John Nemunaitis, Molecular Therapy, 2005, Vol. 11, No. 2, p. 180-195

SUMMARY OF INVENTION

An object of the present invention is to provide a cancer therapy by combination use of oncolytic vaccinia virus and an immune checkpoint inhibitor, and a pharmaceutical composition and a combined medicine for use in the cancer therapy.

The present inventors surprisingly found, in developing combination use of a genetically modified vaccinia virus with another type of cancer therapy, that if vaccinia virus containing two polynucleotides, i.e., a polynucleotide encoding IL-7 and a polynucleotide encoding IL-12, are used in combination with an immune checkpoint inhibitor (for example, anti-PD-1 antibody and anti-CTLA-4 antibody), an excellent antitumor effect is exerted and excellent complete remission induction effect is provided on a remote tumor to which vaccinia virus is not administered (Example 1). Based on the finding, the present invention was accomplished.

According to the present invention, the following inventions are provided.

[1] A pharmaceutical composition comprising vaccinia virus as an active ingredient for use in treating cancer, wherein the vaccinia virus is (1) vaccinia virus comprising a polynucleotide encoding interleukin-7 (IL-7) and vaccinia virus comprising a polynucleotide encoding interleukin-12 (IL-12); or (2) vaccinia virus comprising a polynucleotide encoding interleukin-7 (IL-7) and a polynucleotide encoding interleukin-12 (IL-12) and is to be used in combination with an immune checkpoint inhibitor.

[2] The pharmaceutical composition according to [1], wherein the vaccinia virus is vaccinia virus comprising a polynucleotide encoding IL-7 and a polynucleotide encoding IL-12.

[3] The pharmaceutical composition according to [1] or [2], wherein the vaccinia virus is defective in functions of vaccinia virus growth factors (VGF) and O1L.

[4] The pharmaceutical composition according to [3], wherein the vaccinia virus lacks an SCR (short consensus repeat) domain in a B5R extracellular region.

[5] The pharmaceutical composition according to any one of [1] to [4], wherein the vaccinia virus is vaccinia virus LC16mO strain.

[6] The pharmaceutical composition according to any one of [1] to [5], wherein the immune checkpoint inhibitor is an antibody selected from the group consisting of an anti-PD-1 antibody, an anti-PD-L1 antibody and an anti-CTLA-4 antibody, or an antigen-binding fragment thereof.

[7] The pharmaceutical composition according to any one of [1] to [6], wherein the cancer is solid cancer.

[8] The pharmaceutical composition according to any one of [1] to [7], wherein the cancer is metastatic cancer.

[9] A combined medicine for use in treating cancer, comprising: a pharmaceutical composition comprising vaccinia virus comprising a polynucleotide encoding interleukin-7 (IL-7); and a pharmaceutical composition comprising vaccinia virus comprising a polynucleotide encoding interleukin-12 (IL-12), and to be used in combination with an immune checkpoint inhibitor.

[10] A combined medicine for use in treating cancer, comprising: the pharmaceutical composition according to any one of [1] to [8] or the combined medicine according to [9]; and a pharmaceutical composition comprising an immune checkpoint inhibitor.

[11] A pharmaceutical composition comprising an immune checkpoint inhibitor for use in treating cancer, to be used in combination with the pharmaceutical composition according to any one of [1] to [8] or the combined medicine according to [9].

[12] A method of treating cancer, comprising administering an immune checkpoint inhibitor and a vaccinia virus, wherein the vaccinia virus is (1) vaccinia virus comprising a polynucleotide encoding interleukin-7 (IL-7) and vaccinia virus comprising a polynucleotide encoding interleukin-12 (IL-12); or (2) vaccinia virus comprising a polynucleotide encoding interleukin-7 (IL-7) and a polynucleotide encoding interleukin-12 (IL-12).

[13] A vaccinia virus for use in treating cancer, wherein the vaccinia virus is (1) vaccinia virus comprising a polynucleotide encoding interleukin-7 (IL-7) and vaccinia virus comprising a polynucleotide encoding interleukin-12 (IL-12); or (2) vaccinia virus comprising a polynucleotide encoding interleukin-7 (IL-7) and a polynucleotide encoding interleukin-12 (IL-12); and is to be used in combination with an immune checkpoint inhibitor.

[14] Use of a vaccinia virus for the manufacture of a medicament for use in treating cancer, wherein the vaccinia virus is (1) vaccinia virus comprising a polynucleotide encoding interleukin-7 (IL-7) and vaccinia virus comprising a polynucleotide encoding interleukin-12 (IL-12); or (2) vaccinia virus comprising a polynucleotide encoding interleukin-7 (IL-7) and a polynucleotide encoding interleukin-12 (IL-12); and is to be used in combination with an immune checkpoint inhibitor.

The oncolytic vaccinia virus for use in treating cancer (particularly, oncolytic vaccinia virus containing two polynucleotides, i.e., a polynucleotide encoding IL-7 and a polynucleotide encoding IL-12), if it is used in combination with an immune checkpoint inhibitor (for example, an antibody inhibiting the binding between PD-1 and PD-L1, or anti-CTLA-4 antibody), can further improve its antitumor effect.

BRIEF DESCRIPTION OF THE DRAWING

FIG. 1 shows graphs exhibiting effects (tumor volume and number of mice having complete remission) of combination use of IL-12 and IL-7-carrying vaccinia virus and an anti-PD-1 antibody or an anti-CTLA-4 antibody, in tumor-bearing mice. In each graph, the vertical axis shows the volume of a tumor; whereas the horizontal axis shows the number of days elapsed after grouping of mice based on the volume of cancer cells grafted. In the graphs, reference symbol "CR" represents complete remission, and the number attached to the reference symbol represents the number (expressed by fraction) of mice achieved complete remission per 10 mice. Also, reference symbol "IL-7/IL-12-VV" represents IL-7 and IL-12-carrying vaccinia virus. In each graph, the lines show changes in tumor volume of individual mice over time.

DETAILED DESCRIPTION OF PREFERRED EMBODIMENTS

In the specification, the "subject" refers to a mammal, particularly, a human. The subject can be a subject having cancer, a human having cancer, for example, a human having metastatic cancer. The subject can be a subject having, for example, solid cancer, for example, metastatic solid cancer.

In the specification, then, "combination use" refers to administering a plurality of pharmaceutically active ingredients simultaneously or separately to a same subject, for treatment. In the combination use, the plural pharmaceutically active ingredients may be contained in a same composition or separately in different compositions.

In the specification, the "pharmaceutical composition" refers to a single composition containing a single or a plurality of pharmaceutically active ingredients. The "combined medicine" refers to a combination of different pharmaceutical compositions each containing an active pharmaceutical ingredient.

In the specification, the meaning of "treatment" includes prevention and therapy.

In the specification, the "immune checkpoint inhibitor" refers to a medicinal agent removing suppression of activation of immune cells by an immune checkpoint molecule. Examples of the immune checkpoint molecule include PD-1, CTLA-4, TIM-3 (T-cell immunoglobulin domain and mucin domain-3), LAG-3 (lymphocyte activation gene 3), TIGIT (T cell immunoreceptor with Ig and ITIM domains), BTLA (B and T lymphocyte associated) and VISTA (V-type immunoglobulin domain-containing suppressor of T-cell activation). The immune checkpoint inhibitor binds, for example, to an immune checkpoint molecule or a ligand thereof to inhibit an immunosuppressive signal, and thereby can inhibit the function of an immune checkpoint. For example, a PD-1 signal can be inhibited by inhibiting the binding between PD-1 and PD-L1 or PD-L2. Also, a CTLA-4 signal can be inhibited by inhibiting the binding between CTLA-4 and CD80 or CD86 (Matthieu Collin, Expert Opinion on Therapeutic Patents, 2016, Vol. 26, p. 555-564).

In the specification, the "antibody" refers to an immunoglobulin, which is a biomolecule containing two heavy chains (H chains) and two light chains (L chains) stabilized with disulfide bonds. The heavy chain consists of a heavy chain variable region (VH), heavy chain constant regions (CH1, CH2, CH3) and a hinge region positioned between CH1 and CH2. The light chain consists of a light chain variable region (VL) and a light chain constant region (CL). Of them, a variable region fragment (Fv) consisting of VH and VL is directly involved in binding to an antigen and is the region providing variability to the antibody. The region consisting of the hinge region, CH2 and CH3 is called as Fc region.

In the variable region, the region directly in contact with an antigen is particularly a region having a large variability and called as a complementarity determining region (CDR). The region except CDR having relatively low variability is called as a framework region (FR). The variable regions of a light chain and a heavy chain each have 3 CDRs, which are called as heavy chain CDR1 to CDR3 and light chain CDR1 to CDR3 sequentially from the N terminal.

The antibody may be a monoclonal antibody or a polyclonal antibody and preferably a monoclonal antibody can be used in the present invention. The antibody may be any isotype of IgG, IgM, IgA, IgD or IgE. The antibody may be prepared by immunizing a non-human animal such as a mouse, a rat, a hamster, a guinea pig, a rabbit and a chicken, and may be a recombinant antibody, a chimeric antibody, a humanized antibody and a human antibody. The chimeric antibody herein refers to an antibody prepared by connecting antibody fragments derived from different species. The humanized antibody refers to an antibody prepared by replacing CDRs of a human antibody respectively for the corresponding CDRs of an antibody of a non-human animal (for example, non-human mammal). The humanized antibody is an antibody having CDRs derived from a non-human animal and the other region of the antibody derived from a human. The human antibody is also called as a complete human antibody and individual portions of the human antibody all consist of amino acid sequences encoded by human antibody genes. In the present invention, a chimeric antibody can be used in an embodiment, a humanized antibody in another embodiment and a human antibody (complete human antibody) in a further another embodiment.

In the specification, the "antigen-binding fragment" refers to an antibody fragment that can bind to an antigen. Examples of the antigen-binding fragment include Fab consisting of VL, VH, CL and CH1 regions; F(ab')2 formed of two Fab fragments connected at the hinge region with a disulfide bond; Fv formed of VL and VH, a single-chain antibody, scFv, prepared by connecting VL and VH with an artificial polypeptide linker; bispecific antibodies such as a diabody, a single chain diabody (scDb), tandem scFv and leucine zipper; and a heavy chain antibody such as VHH antibody (MAbs, 2017, Vol. 9, No. 2, p. 182-212).

According to the present invention, a single or a plurality of vaccinia viruses are prepared by integrating polynucleotides encoding IL-7 and IL-12 therein so as to be expressed and used in combination with an immune checkpoint inhibitor. In this manner, treatment of cancer can be expected according to the present invention.

Now, each of the constitutional elements of the inventions will be described, below.

Vaccinia Virus that Can Be Used in the Present Invention

A single or a plurality of vaccinia viruses that can be used in the present invention can contain the following (1) and (2):
(1) a polynucleotide encoding IL-7, and
(2) a polynucleotide encoding IL-12.
(In the specification, the vaccinia virus will be hereinafter referred also to "the vaccinia virus to be used in the present invention").

In the present invention, the polynucleotides (1) and (2) may be contained in a single vaccinia virus or separately in a plurality of vaccinia viruses.

In an embodiment, the vaccinia virus to be used in the present invention contains a polynucleotide encoding IL-7 and a polynucleotide encoding IL-12.

In an embodiment, the vaccinia virus to be used in the present invention is vaccinia virus containing a polynucleotide encoding IL-7 and vaccinia virus containing a polynucleotide encoding IL-12.

When a polynucleotide encoding IL-7 and a polynucleotide encoding IL-12 are contained separately in a plurality of vaccinia viruses, the plural vaccinia viruses may be contained in a single pharmaceutical composition or may be in the form of a combined medicine in which the vaccinia viruses are separately contained in different pharmaceutical compositions.

In an embodiment, the vaccinia virus to be used in the present invention is vaccinia virus containing a polynucleotide encoding IL-7, which is to be used in combination with vaccinia virus containing a polynucleotide encoding IL-12. In an embodiment, the vaccinia virus to be used in the present invention is also vaccinia virus containing a polynucleotide encoding IL-12, which is to be used in combination with vaccinia virus containing a polynucleotide encoding IL-7.

The vaccinia virus to be used in the present invention is a virus belonging to the orthopoxvirus genus of the poxvirus family. Examples of the strain of the vaccinia virus to be used in the present invention include, but are not limited to, Lister strain, New York City Board of Health (NYBH) strain, Wyeth strain, Copenhagen strain, Western Reserve (WR) strain, EM63 strain, Ikeda strain, Dairen strain and Tian Tan strain. Lister strain is available from the American type Culture Collection (ATCC VR-1549). Further, as the vaccinia virus to be used in the present invention, established vaccinia virus strains derived from these strains can be used. For example, as the vaccinia virus to be used in the present invention, LC16 strain, LC16m8 strain and LC16mO strain established from Lister strain can be used. LC16mO strain is a strain produced via LC16 strain, which is obtained by subculture of Lister strain used as a parent strain at a low temperature. LC16m8 strain is a strain produced by further subculturing LC16mO strain at a low temperature and an attenuated strain since a frame-shift mutation occurs in B5R gene encoding a viral membrane protein, with the result that the protein is not expressed and loses its function (Protein, Nucleic acid and Enzyme, 2003, Vol. 48, p. 1693-1700). As the whole genome sequences of Lister strain, LC16m8 strain and LC16mO strain, for example, Accession No. AY678276.1, Accession No. AY678275.1 and Accession No. AY678277.1 are respectively known. Accordingly, LC16m8 strain and LC16mO strain can be prepared from Lister strain by homologous recombination and site-directed mutagenesis known in the art.

In an embodiment, the vaccinia virus to be used in the present invention is vaccinia virus LC16mO strain.

As the vaccinia virus to be used in the present invention, an attenuated and/or tumor-selective vaccinia virus can be used. In the specification, the "attenuated" means that toxicity (for example, cytolytic property) to normal cells (for example, nontumor cells) is low. In the specification, the "tumor selectivity" means that toxicity (for example, oncolytic property) to tumor cells is higher than to normal cells. As the vaccinia virus to be used in the present invention, genetically modified vaccinia virus defective in the function of a predetermined protein and suppressed in expression of a predetermined gene or protein, can be used (Expert Opinion on Biological Therapy, 2011, Vol. 11, p. 595-608). For example, vaccinia virus defective in function of thymidine kinase (TK) (Cancer Gene Therapy, 1999, Vol. 6, p. 409-422), which is modified to improve the tumor selectivity of vaccinia virus; vaccinia virus defective in function of vaccinia virus growth factor (VGF) (Cancer Research, 2001, Vol. 61, p. 8751-8757); vaccinia virus containing a modified TK gene, a modified hemagglutinin (HA) gene and a modified F3 gene or an interrupted F3 locus (WO 2005/047458); vaccinia virus defective in functions of VGF and On (WO 2015/076422); vaccinia virus prepared by inserting a micro RNA target sequence decreased in expression in cancer cells in the 3' untranslated region of B5R gene (WO 2011/125469); vaccinia virus defective in functions of VGF and TK (Cancer Research, 2001, Vol. 61, p. 8751-8757); vaccinia virus defective in functions of TK, HA and F14.5L (Cancer Research, 2007, Vol. 67, p. 10038-10046); vaccinia virus defective in functions of TK and B18R (PLoS Medicine, 2007, Vol. 4, p. e353); vaccinia virus defective in functions of TK and ribonucleotide reductase (PLoS Pathogens, 2010, Vol. 6, p. e1000984); vaccinia virus defective in functions of SPI-1 and SPI-2 (Cancer Research, 2005, Vol. 65, p. 9991-9998); vaccinia virus defective in functions of SPI-1, SPI-2 and TK (Gene Therapy, 2007, Vol. 14, p. 638-647); or vaccinia virus having mutations in E3L and K3L regions (WO 2005/007824), can be used. Also, vaccinia virus defective in function of O1L can be used (Journal of Virology, 2012, Vol. 86, p. 2323-2336). Also, vaccinia virus defective in the B5R extracellular region (Virology, 2004, Vol. 325, p. 425-431) or vaccinia virus defective in A34R region (Molecular Therapy, 2013, Vol. 21, p. 1024-1033) prepared in order that elimination of virus in vivo by neutralization effect of anti-vaccinia virus antibody is expectedly attenuated, can be used. Also, vaccinia virus defective in interleukin-1b (IL-1b) receptor prepared in order that immune cells are expectedly activated by vaccinia virus (WO 2005/030971) can be used. Insertion of these foreign genes, deletion and mutation of genes can be carried out, for example, by homologous recombination and site-directed mutagenesis known in the art. In the present invention, vaccinia virus having these genetic modifications in combination can be used. In the specification, the "defective" means that the gene region specified by this term is not functioned, including the case where the gene region is deleted. For example, the "defective" means that a deletion may occur in the region consisting of the specified gene region or in the peripheral gene region including the specified gene region.

In an embodiment, the vaccinia virus to be used in the present invention is defective in VGF function. In an embodiment, the vaccinia virus to be used in the present invention is defective in O1L function. In an embodiment, the vaccinia virus to be used in the present invention is defective in VGF and O1L functions. The VGF and/or O1L functions can be deleted from vaccinia virus based on the description of WO 2015/076422.

VGF is a protein having a high homology with the amino acid sequence of epidermal growth factor (EGF) and binds to the epidermal growth factor receptor similarly to EGF and activates the signal cascade starting from Ras, Raf, mitogen-activated protein kinase (MAPK)/extracellular signal-regulated kinase (ERK) kinase (MAPK/ERK kinase, MEK) and continued to ERK to facilitate cell division.

O1L maintains activation of ERK and contributes to cell division, together with VGF.

Defective in function of VGF and/or O1L of vaccinia virus means that neither a gene encoding VGF nor a gene encoding O1L is expressed, or either one of them is not expressed, or that even if the genes are expressed, the expressed proteins fail to have normal function(s) of VGF and/or O1L. In order that the function(s) of VGF and/or O1L of vaccinia virus is made defective, whole or part of a gene encoding VGF and/or a gene encoding O1L may be deleted. Alternatively, a nucleotide(s) may be substituted, deleted, inserted or added to mutate the gene so as not to express normal VGF and/or O1L. Alternatively, a foreign gene may be inserted in the gene(s) encoding VGF and/or the gene encoding O1L. In the present invention, if a normal gene product is not expressed by mutation of a gene due to, e.g., substitution, deletion, insertion or addition, it is said that gene is defective.

Whether VGF and/or O1L function is defective or not in the vaccinia virus to be used in the present invention can be determined by a method known in the art; for example, functional evaluation of VGF and/or O1L, confirmation of the presence of VGF or O1L by an immunochemical method using an antibody against VGF or an antibody against O1L, and determination of the presence of a gene encoding VGF and a gene encoding O1L by polymerase chain reaction (PCR) (Cancer Research, 2001, Vol. 61, p. 8751-8757).

In an embodiment, the vaccinia virus to be used in the present invention is vaccinia virus LC16mO strain defective in VGF and O1L functions.

B5R (Accession No. AAA48316.1) is a Type-1 membrane protein present in the envelope of vaccinia virus and has a function to enhance infection efficiency of the virus when the virus infects or transmits to adjacent cells or other sites within a host. In the B5R extracellular region, 4 structures called as SCR (short consensus repeat) domains are present (Journal of Virology, 1998, Vol. 72, p. 294-302). In an embodiment, in the vaccinia virus to be used in the present invention, an SCR domain(s) of the B5R extracellular region is deleted.

Deletion of SCR domain in the B5R extracellular region of vaccinia virus include deletion of a whole or part of 4 SCR domains in the B5R extracellular region, and means that a gene region encoding a part or whole of the 4 SCR domains in the B5R extracellular region is not expressed or the B5R protein expressed does not have a part or whole of the 4 SCR domains in the extracellular region. In an embodiment, in vaccinia virus to be used in the present invention, the 4 SCR domains of B5R are deleted. In an embodiment, 4 SCR domains deleted in the vaccinia virus to be used in the present invention is the region in the B5R extracellular region corresponding to the 22nd to 237th amino acids in the amino acid sequence as shown in Accession No. AAA48316.1.

Whether the SCR domain(s) of the B5R extracellular region is deleted or not in the vaccinia virus to be used in the present invention can be determined by a method known in the art, for example, by confirming the presence of an SCR domain(s) by an immunochemical method using an antibody against an SCR domain and determining the presence of a gene encoding an SCR domain(s) or the size thereof by PCR.

In an embodiment, the vaccinia virus to be used in the present invention is vaccinia virus defective in functions of VGF and O1L and lacking an SCR domain(s) of the B5R extracellular region.

In an embodiment, the vaccinia virus to be used in the present invention is vaccinia virus LC16mO strain defective in functions of VGF and O1L and lacking an SCR domain(s) of the B5R extracellular region.

In an embodiment, the vaccinia virus to be used in the present invention is vaccinia virus containing a polynucleotide encoding IL-7 and a polynucleotide encoding IL-12 and defective in VGF and O1L functions.

In an embodiment, the vaccinia virus to be used in the present invention is vaccinia virus LC16mO strain containing a polynucleotide encoding IL-7 and a polynucleotide encoding IL-12 and defective in VGF and O1L functions.

In an embodiment, the vaccinia virus to be used in the present invention is vaccinia virus containing a polynucleotide encoding IL-7 and a polynucleotide encoding IL-12, defective in VGF and O1L functions and lacking an SCR domain(s) of the B5R extracellular region.

In an embodiment, the vaccinia virus to be used in the present invention is vaccinia virus LC16mO strain containing a polynucleotide encoding IL-7 and a polynucleotide encoding IL-12, defective in VGF and O1L functions and lacking an SCR domain(s) of the B5R extracellular region.

In an embodiment, the vaccinia virus to be used in the present invention is vaccinia virus containing a polynucleotide encoding IL-7 and defective in VGF and O1L functions, and to be used in combination with vaccinia virus containing a polynucleotide encoding IL-12. In an embodiment, the vaccinia virus to be used in the present invention is vaccinia virus containing a polynucleotide encoding IL-12 and defective in VGF and O1L functions, and to be used in combination with vaccinia virus containing a polynucleotide encoding IL-7.

In an embodiment, the vaccinia virus to be used in the present invention is vaccinia virus LC16mO strain containing a polynucleotide encoding IL-7 and defective in VGF and O1L functions, and to be used in combination with vaccinia virus containing a polynucleotide encoding IL-12. In an embodiment, the vaccinia virus to be used in the present invention is vaccinia virus LC16mO strain containing a polynucleotide encoding IL-12 and defective in VGF and O1L functions, and to be used in combination with vaccinia virus containing a polynucleotide encoding IL-7.

In an embodiment, the vaccinia virus to be used in the present invention is vaccinia virus containing a polynucleotide encoding IL-7, defective in VGF and O1L functions, lacking an SCR domain(s) of the B5R extracellular region, and to be used in combination with vaccinia virus containing a polynucleotide encoding IL-12. In an embodiment, the vaccinia virus to be used in the present invention is vaccinia virus containing a polynucleotide encoding IL-12, defective in VGF and O1L functions, lacking an SCR domain(s) of the B5R extracellular region and to be used in combination with vaccinia virus containing a polynucleotide encoding IL-7.

In an embodiment, the vaccinia virus to be used in the present invention is vaccinia virus LC16mO strain containing a polynucleotide encoding IL-7, defective in VGF and O1L functions, lacking an SCR domain(s) of the B5R extracellular region, and to be used in combination with vaccinia virus containing a polynucleotide encoding IL-12. In an embodiment, the vaccinia virus to be used in the present invention is vaccinia virus LC16mO strain containing a polynucleotide encoding IL-12, defective in VGF and O1L functions, lacking an SCR domain(s) of the B5R extracellular region, and to be used in combination with vaccinia virus containing a polynucleotide encoding IL-7.

IL-7 is a secretory protein serving as an agonist to an IL-7 receptor. IL-7 is reported to contribute to survival, proliferation and differentiation of, e.g., T cells and B cells (Current Drug Targets, 2006, Vol. 7, p. 1571-1582). In the present invention, IL-7 includes naturally occurring IL-7 and a variant having its function. In an embodiment, IL-7 is human IL-7. In the present invention, human IL-7 includes naturally occurring human IL-7 and a variant having its function. In an embodiment, human IL-7 is selected from the group consisting of the following (1) to (3):

(1) a polypeptide containing the amino acid sequence as shown in Accession No. NP_000871.1 and having the function of human IL-7, (2) a polypeptide consisting of an amino acid sequence having a deletion, substitution, insertion, and/or addition of 1 to 10 amino acids in the amino acid sequence as shown in Accession No. NP_000871.1, and having the function of human IL-7, and (3) a polypeptide containing an amino acid sequence having an identity of 90% or more with the amino acid sequence as shown in Accession No. NP_000871.1 and having the function of human IL-7.

The function of human IL-7 herein refers to a function responsible for survival, proliferation and differentiation action of various human immune cells.

In an embodiment, human IL-7 used in the present invention is a polypeptide consisting of the amino acid sequence as shown in Accession No. NP_000871.1.

IL-12 is a heterodimer consisting of IL-12 subunit p40 and IL-12 subunit α. IL-12 is reported to have a function to activate and induce differentiation of T cells and NK cells (Cancer Immunology Immunotherapy, 2014, Vol. 63, p. 419-435). In the present invention, IL-12 includes naturally occurring IL-12 and a variant having its function. In an embodiment, IL-12 is human IL-12. In the present invention, human IL-12 includes naturally occurring human IL-12 and a variant having its function. In an embodiment, human IL-12, as a combination of human IL-12 subunit p40 and human IL-12 subunit α, is selected from the group consisting of the following (1) to (3):

(1)

(i-1) a polypeptide containing the amino acid sequence as shown in Accession No. NP_002178.2, (i-2) a polypeptide consisting of an amino acid sequence having a deletion, substitution, insertion, and/or addition of 1 to 10 amino acids in the amino acid sequence as shown in Accession No. NP_002178.2, or (i-3) a polypeptide containing an amino acid sequence having an identity of 90% or more with the amino acid sequence as shown in Accession No. NP_002178.2, and (ii-1) a polypeptide containing the amino acid sequence as shown in Accession No. NP_000873.2, (ii-2) a polypeptide consisting of an amino acid sequence having a deletion, substitution, insertion, and/or addition of 1 to 10 amino acids in the amino acid sequence as shown in Accession No. NP_000873.2, or (ii-3) a polypeptide containing an amino acid sequence having an identity of 90% or more with the amino acid sequence as shown in Accession No. NP_000873.2, and having a function of human IL-12, (2)

(i-1) a polypeptide consisting of the amino acid sequence as shown in Accession No. NP_002178.2, (ii-1) a polypeptide containing the amino acid sequence as shown in Accession No. NP_000873.2, (ii-2) a polypeptide consisting of an amino acid sequence having a deletion, substitution, insertion, and/or addition of 1 to 10 amino acids in the amino acid sequence as shown in Accession No. NP_000873.2, or (ii-3) a polypeptide containing the amino acid sequence having an identity of 90% or more with the amino acid sequence as shown in Accession No. NP_000873.2, and having a function of human IL-12, and, (3)

(i-1) a polypeptide containing the amino acid sequence as shown in Accession No. NP_002178.2, (i-2) a polypeptide consisting of an amino acid sequence having a deletion, substitution, insertion, and/or addition of 1 to 10 amino acids in the amino acid sequence as shown in Accession No. NP_002178, or (i-3) a polypeptide containing the amino acid sequence having an identity of 90% or more with the amino acid sequence as shown in Accession No. NP_002178.2, and (ii-1) a polypeptide consisting of the amino acid sequence as shown in Accession No. NP_000873.2, and having the function of human IL-12.

The function of human IL-12 herein refers to a function to activate and/or induce differentiation of T cells and NK cells. IL-12 subunit p40 and IL-12 subunit α can be directly bound to each other to form IL-12. Alternatively, IL-12 subunit p40 and IL-12 subunit α can be bound through a linker.

In an embodiment, human IL-12 to be used in the present invention is a polypeptide, including a polypeptide(s) consisting of the amino acid sequence as shown in Accession No. NP_002178.2 and a polypeptide consisting of the amino acid sequence as shown in Accession No. NP_000873.2.

In the specification, the "identity" refers to an identity value obtained in accordance with EMBOSS Needle (Nucleic Acids Res., 2015, Vol. 43, p. W580-W584) using parameters prepared by default. The parameters are as follows:

Gap Open Penalty=10
Gap Extend Penalty=0.5
Matrix=EBLOSUM62
End Gap Penalty=false.

The vaccinia virus to be used in the present invention has oncolytic activity. A method for evaluating whether a test virus has an oncolytic activity or not includes a method of evaluating a decrease in survival rate of cancer cells by addition of the virus. Examples of the cancer cells to be used for evaluation include malignant melanoma cells RPMI-7951 (for example, ATCC HTB-66), lung adenocarcinoma cells HCC4006 (for example, ATCC CRL-2871), lung cancer cells A549 (for example, ATCC CCL-185), small cell lung cancer cells DMS 53 (for example, ATCC CRL-2062), lung squamous cell carcinoma cells NCI-H226 (for example, ATCC CRL-5826), kidney cancer cells Caki-1 (for example, ATCC HTB-46), bladder cancer cells 647-V (for example, DSMZ ACC 414), head and neck cancer cells Detroit 562 (for example, ATCC CCL-138), breast cancer cells JIMT-1 (for example, DSMZ ACC 589), breast cancer cells MDA-MB-231 (for example, ATCC HTB-26), esophageal cancer cells OE33 (for example, ECACC 96070808), glioblastoma U-87MG (for example, ECACC 89081402), neuroblastoma GOTO (for example, JCRB JCRB0612), myeloma RPMI 8226 (for example, ATCC CCL-155), ovarian cancer cells SK-OV-3 (for example, ATCC HTB-77), ovarian cancer cells OVMANA (for example, JCRB JCRB1045), colon cancer cells RKO (for example, ATCC CRL-2577), colon cancer cells HCT 116 (for example, ATCC CCL-247), pancreatic cancer cells BxPC-3 (for example, ATCC CRL-1687), prostate cancer cells LNCaP clone FGC (for example, ATCC CRL-1740), liver cancer cells JHH-4 (for example, JCRB JCRB0435), mesothelioma NCI-H28 (for example, ATCC CRL-5820), cervical cancer cells SiHa (for example, ATCC HTB-35) and stomach cancer cells Kato III (for example, RIKEN BRC RCB2088).

The vaccinia virus to be used in the present invention produces IL-7 and/or IL-12 polypeptides in the infected cell. If the vaccinia virus to be used in the present invention is used, IL-7 and IL-12 polypeptides are produced. Due to the production, the antitumor effect is markedly improved. Production of IL-7 and IL-12 can be confirmed by a method known in the art, for example, by culturing vaccinia virus having polynucleotides encoding each polypeptide of IL-7 and IL-12 introduced therein together with cancer cells, and thereafter, measuring the concentrations of IL-7 and IL-12 in the culture supernatant, performing immunostaining of a cell or western blot analysis of a cell lysate, or measuring the concentrations of IL-7 and IL-2 in a cell lysate. The concentrations of IL-7 and IL-12 can be determined, for example, by use of Human IL-7 ELISA kit (Ray Biotech, Inc.) and Human IL-12 p70 DuoSet ELISA (R&D Systems, Inc.), respectively. Cell immunostaining or western blot analysis of a cell lysate of IL-7 and IL-12 can be carried out by using a commercially available anti-IL-7 antibody and an anti-IL-12 antibody, respectively.

The respective polynucleotides encoding IL-7 and IL-12 can be synthesized in accordance with a polynucleotide synthesis method known in the art based on sequence information available publicly. Once the individual polynucleotides are obtained, it is possible to prepare variants having the functions of the individual polypeptides by introducing a mutation into a predetermined site by using a method known to those skilled in the art, such as site-directed mutagenesis (Current Protocols in Molecular Biology edition, 1987, John Wiley & Sons Section 8.1-8.5).

Respective polynucleotides encoding IL-7 and IL-12 can be introduced into vaccinia virus by homologous recombination and site-directed mutagenesis known in the art. For example, a plasmid (also referred to as transfer vector plasmid DNA) is prepared by introducing the polynucleotide(s) into the nucleotide sequence of a desired site to be introduced and can be introduced into cells infected with vaccinia virus. In an embodiment, the region to which foreign genes, i.e., respective polynucleotides encoding IL-7 and IL-12, are to be introduced, is a gene region not essential for the life cycle of vaccinia virus. For example, in an embodiment, IL-7 and/or IL-12 introduction region(s) in VGF function-defective vaccinia virus can be specified as the interior of the VGF gene; the region(s) in O1L function-defective vaccinia virus, can be specified as the interior of the O1L gene, the region(s) in vaccinia virus defective in both VGF function and O1L function can be specified as the interior of either one or both of the VGF gene and O1L gene. In the above, foreign genes can be introduced such that they are transcribed in a direction same or opposite to the transcription directions of VGF and O1L genes.

Examples of the method for introducing the transfer vector plasmid DNA into cells include, but are not particularly limited to, a calcium phosphate method and an electroporation method.

In introducing respective polynucleotides encoding IL-7 and IL-12 as foreign genes, appropriate promoters can be operatively linked to a upstream site of the foreign genes. In this manner, in vaccinia virus to be used in the present invention, the foreign genes can be linked to promoters expressible in tumor cells. Examples of these promoters include PSFJ1-10, PSFJ2-16, p7.5K promoter, p11K promoter, T7.10 promoter, CPX promoter, HF promoter, H6 promoter and T7 hybrid promoter.

In an embodiment, the vaccinia virus to be used in the present invention does not have a drug selection marker gene.

The vaccinia virus to be used in the present invention can be expressed and/or proliferated by infecting host cells with vaccinia virus and culturing infected host cells. The vaccinia virus can be expressed and/or proliferated in accordance with a method known in the art. As the host cells to be used for expression or proliferation of the vaccinia virus to be used in the present invention are not particularly limited as long as the vaccinia virus to be used in the present invention can be expressed and proliferated therein. Examples of the host cells include animal cells such as BS-C-1, A549, RK13, HTK-143, Hep-2, MDCK, Vero, HeLa, CV-1, COS, BHK-21, and primary rabbit kidney cells. In an embodiment, BS-C-1 (ATCC CCL-26), A549 (ATCC CCL-185), CV-1 (ATCC CCL-70) or RK13 (ATCC CCL-37) can be used. The culture conditions for host cells such as temperature, pH of a culture medium and culture time, are appropriately selected.

In a method for producing the vaccinia virus to be used in the present invention, in addition to steps of infecting host cells with the vaccinia virus to be used in the present invention, culturing the infected host cells and expressing the vaccinia virus to be used in the present invention, a step of collecting, preferably, purifying the vaccinia virus to be used in the present invention can be further included. As the purification method, DNA digestion with Benzonase, sucrose gradient centrifugation, iodixanol density gradient centrifugation, ultrafiltration and diafiltration can be used.

Immune Checkpoint Inhibitor that Can Be Used in the Present Invention

In the present invention, as the immune checkpoint inhibitor, for example, checkpoint inhibitors that block a signal through PD-1 or checkpoint inhibitors that block a signal through CTLA-4 can be used. As the immune checkpoint inhibitor, an antibody that can neutralize the binding between PD-1 and PD-L1 or PD-L2 and an antibody that can neutralize the binding between CTLA-4 and CD80 or CD86, can be mentioned. The antibody neutralizing the binding between PD-1 and PD-L1 includes an anti-PD-1 antibody and an anti-PD-L1 antibody that can neutralize the binding between PD-1 and PD-L1. The antibody neutralizing the binding between PD-1 and PD-L2 includes an anti-PD-1 antibody and an anti-PD-L2 antibody that can neutralize the binding between PD-1 and PD-L2. The antibody that can neutralize the binding between CTLA-4 and CD80 or CD86 includes an anti-CTLA-4 antibody neutralizing the binding between CTLA-4 and CD80 or CD86.

Examples of the immune checkpoint inhibitors that can be used in the present invention include, but are not particularly limited to, an anti-PD-1 antibody such as nivolumab, pembrolizumab and pidilizumab; an anti-PD-L1 antibody such as atezolizumab, durvalumab and avelumab; an anti-CTLA-4 antibody such as ipilimumab, an anti-TIM-3 antibody such as TSR-022 (WO 2016/161270) and MBG453 (WO 2015/117002); an anti-LAG-3 antibody such as LAG525 (US 2015/0259420A), an anti-TIGIT antibody such as MAB10 (WO 2017/059095), an anti-BTLA antibody such as BTLA-8.2 (The Journal of Clinical Investigation, 2010, Vol. 120: No. 1, p. 157-167) and an anti-VISTA antibody such as JNJ-61610588 (WO 2016/207717). Examples of the immune checkpoint inhibitors that can be used in the present invention include cells producing an antigen-binding fragment binding to an immune checkpoint molecule or a ligand thereof, a vector expressing an antigen-binding fragment in vivo and a low molecular-weight compound that suppress the immunosuppressive signal.

In the present invention, the above immune checkpoint inhibitor can be used in combination with the vaccinia virus to be used in the present invention. Also, in the present invention, the above immune checkpoint inhibitor can be used in combination with a combined medicine of the vaccinia virus to be used in the present invention.

In an embodiment, the immune checkpoint inhibitor to be used in the present invention is an antibody selected from the group consisting of an anti-PD-1 antibody, an anti-PD-L1 antibody and an anti-CTLA-4 antibody or an antigen-binding fragment thereof.

The antibody neutralizing the binding between two proteins can be obtained by obtaining antibodies binding to either one of the two proteins and selecting the obtained antibodies based on the ability to neutralize the binding between the two proteins. For example, an antibody that can neutralize the binding between PD-1 and PD-L1 can be obtained by obtaining antibodies binding to either one of PD-1 and PD-L1, and then, selecting the obtained antibody based on the ability to neutralize the binding between PD-1 and PD-L1. Also, for example, an antibody that can neutralize the binding between PD-1 and PD-L2 can be obtained by obtaining antibodies binding to either one of PD-1 and PD-L2, and then, selecting the obtained antibody based on the ability to neutralize the binding between PD-1 and PD-L2. Also, for example, an antibody that can neutralize the binding between CTLA-4 and CD80 or CD86 can be obtained by obtaining antibodies binding to CTLA-4, and then, selecting the obtained antibody based on the ability to neutralize the binding between CTLA-4 and CD80 or CD86. The antibody binding to a protein can be obtained, for example, by a method known to those skilled in the art. Also, the ability of an antibody to neutralize the binding between two proteins can be checked by immobilizing one of the two proteins, adding the other protein in a liquid phase, and then checking whether the binding amount of the antibody decreases or not. For example, a label is attached to the protein contained in a liquid phase and if the amount of the label decreases by addition of the antibody, it can be determined that the antibody can neutralize the binding between the two proteins.

PD-1 is a protein having a name of programmed cell death-1 and sometimes called also as PDCD1 or CD279. PD-1, which is a membrane protein of the immunoglobulin superfamily, binds to PD-L1 or PD-L2 to suppress activation of T cells. PD-1 conceivably prevents an autoimmune disease. In cancer cells, PD-L1 is expressed on the cell surface and down-regulates T cells. Owing to this, the cancer cells get rid of attack from T cells. As PD-1, human PD-1 (for example, PD-1 having the amino acid sequence registered under Accession No. NP_005009.1 in Genbank) is mentioned. PD-1 includes PD-1 having the amino acid sequence corresponding to the amino acid sequence registered under Accession No. NP_005009.1 in Genbank. In the specification, "the amino acid sequence corresponding to" is used such that the expression includes functionally equivalent PD-1 including an orthologue and naturally occurring one although the amino acid sequence is not completely identical.

PD-L1 is a ligand for PD-1 and sometimes called also as B7-H1 or CD274. PD-L1 includes, for example, human PD-L1 (for example, PD-L1 having the amino acid sequence registered under Accession No. NP_054862.1 in Genbank). PD-L1 includes PD-L1 having the amino acid sequence corresponding to the amino acid sequence registered under Accession No. NP_054862.1 in Genbank, is mentioned.

PD-L2 is a ligand for PD-1 and sometimes called also as B7-DC or CD273. PD-L2 includes, for example, human PD-L2 (for example, PD-L2 having the amino acid sequence registered under Accession No. AAI13681.1 in Genbank). PD-L2 includes PD-L2 having the amino acid sequence corresponding to the amino acid sequence registered under Accession No. AAI13681.1, is mentioned.

CTLA-4 is a membrane protein of the immunoglobulin superfamily and expressed in activated T cells. CTLA-4 is analogous to CD28 and binds to CD80 and CD86 on antigen presenting cells. It is known that CD28 sends a costimulatory signal to T cells; whereas CTLA-4 sends an inhibitory signal to T cells. CTLA-4 includes, for example, human CTLA-4 (for example, CTLA-4 having the amino acid sequence registered under Accession No. AAH74893.1 in Genbank). CTLA-4 includes CTLA-4 having the amino acid sequence corresponding to the amino acid sequence registered under Accession No. AAH74893.1.

CD80 and CD86 are membrane proteins of the immunoglobulin superfamily expressed on various hematopoietic cells and interact with CD28 and CTLA-4 on the surface of T cells, as described above. CD80 includes, for example, human CD80 (for example, CD80 having the amino acid sequence registered under Accession No. NP_005182.1 in Genbank). CD80 includes CD80 having the amino acid sequence corresponding to the amino acid sequence registered under Accession No. NP_005182.1. CD86 includes, for example, human CD86 (for example, CD86 having the amino acid sequence registered under Accession No. NP_787058.4 in Genbank). CD86 includes human CD86 (for example, CD86 having the amino acid sequence corresponding to the amino acid sequence registered under Accession No. NP_787058.4 in Genbank.

Pharmaceutical Composition and Combined Medicine of the Present Invention

According to the present invention, either one of the following pharmaceutical compositions and combined medicines (hereinafter sometimes referred to as "the pharmaceutical composition and combined medicine of the present invention") can be provided.

(a-1) a pharmaceutical composition for use in treating cancer, containing vaccinia virus containing a polynucleotide encoding IL-7, vaccinia virus containing a polynucleotide encoding IL-12 and an immune checkpoint inhibitor;

(a-2) a pharmaceutical composition for use in treating cancer, containing vaccinia virus containing a polynucleotide encoding IL-7 and a polynucleotide encoding IL-12 and an immune checkpoint inhibitor;

(b-1) a pharmaceutical composition for use in treating cancer, containing vaccinia virus containing a polynucleotide encoding IL-7, and to be used in combination with vaccinia virus containing a polynucleotide encoding IL-12 and an immune checkpoint inhibitor {wherein, the vaccinia virus containing a polynucleotide encoding IL-12 and immune checkpoint inhibitor may be contained in the same pharmaceutical composition and separately in different pharmaceutical compositions};

(b-2) a pharmaceutical composition for use in treating cancer, containing vaccinia virus containing a polynucleotide encoding IL-12, and to be used in combination with vaccinia virus containing a polynucleotide encoding IL-7 and an immune checkpoint inhibitor {wherein, the vaccinia virus containing a polynucleotide encoding IL-7 and immune checkpoint inhibitor may be contained in the same pharmaceutical composition and separately in different pharmaceutical compositions};

(b-3) a pharmaceutical composition for use in treating cancer, containing vaccinia virus containing a polynucleotide encoding IL-7 and a polynucleotide encoding IL-12, and to be used in combination with an immune checkpoint inhibitor;

(b-4) a pharmaceutical composition for use in treating cancer, containing vaccinia virus containing a polynucleotide encoding IL-7 and vaccinia virus containing a polynucleotide encoding IL-12, and to be used in combination with an immune checkpoint inhibitor;

(b-5) a pharmaceutical composition for use in treating cancer, containing vaccinia virus containing a polynucleotide encoding IL-7 and an immune checkpoint inhibitor, and to be used in combination with vaccinia virus containing a polynucleotide encoding IL-12;

(b-6) a pharmaceutical composition for use in treating cancer, containing vaccinia virus containing a polynucleotide encoding IL-12 and an immune checkpoint inhibitor, and to be used in combination with vaccinia virus containing a polynucleotide encoding IL-7;

(b-7) a pharmaceutical composition for use in treating cancer, containing an immune checkpoint inhibitor, and to be used in combination with vaccinia virus containing a polynucleotide encoding IL-7 and a polynucleotide encoding IL-12;

(b-8) a pharmaceutical composition for use in treating cancer, containing an immune checkpoint inhibitor, and to be used in combination with vaccinia virus containing a polynucleotide encoding IL-7 and vaccinia virus containing a polynucleotide encoding IL-12 {wherein, the vaccinia virus containing a polynucleotide encoding IL-7 and vaccinia virus containing a polynucleotide encoding IL-12 may be contained in the same pharmaceutical composition and separately in different pharmaceutical compositions};

(c-1) a combined medicine for use in treating cancer, containing a pharmaceutical composition containing vaccinia virus containing a polynucleotide encoding IL-7, a pharmaceutical composition containing vaccinia virus containing a polynucleotide encoding IL-12 and a pharmaceutical composition containing an immune checkpoint inhibitor;

(c-2) a combined medicine for use in treating cancer, containing a pharmaceutical composition containing vaccinia virus containing a polynucleotide encoding IL-7 and vaccinia virus containing a polynucleotide encoding IL-12 and a pharmaceutical composition containing an immune checkpoint inhibitor;

(c-3) a combined medicine for use in treating cancer, containing a pharmaceutical composition containing vaccinia virus containing a polynucleotide encoding IL-7 and a polynucleotide encoding IL-12 and a pharmaceutical composition containing an immune checkpoint inhibitor;

(c-4) a combined medicine for use in treating cancer, containing a pharmaceutical composition containing vaccinia virus containing a polynucleotide encoding IL-7 and an immune checkpoint inhibitor and a pharmaceutical composition containing vaccinia virus containing a polynucleotide encoding IL-12;

(c-5) a combined medicine for use in treating cancer, containing a pharmaceutical composition containing vaccinia virus containing a polynucleotide encoding IL-12 and an immune checkpoint inhibitor and a pharmaceutical composition containing vaccinia virus containing a polynucleotide encoding IL-7;

(d-1) a combined medicine for use in treating cancer, containing a pharmaceutical composition containing vaccinia virus containing a polynucleotide encoding IL-7 and a pharmaceutical composition containing vaccinia virus containing a polynucleotide encoding IL-12 to be used in combination with an immune checkpoint inhibitor;

(d-2) a combined medicine for use in treating cancer, containing a pharmaceutical composition containing vaccinia virus containing a polynucleotide encoding IL-7 and a pharmaceutical composition containing an immune checkpoint inhibitor and to be used in combination with vaccinia virus containing a polynucleotide encoding IL-12;

(d-3) a combined medicine for use in treating cancer, containing a pharmaceutical composition containing vaccinia virus containing a polynucleotide encoding IL-12 and a pharmaceutical composition containing an immune checkpoint inhibitor and to be used in combination with vaccinia virus containing a polynucleotide encoding IL-7.

In an embodiment, the pharmaceutical composition of the present invention is a pharmaceutical composition for use in treating cancer, containing vaccinia virus as an active ingredient, in which vaccinia virus is (1) vaccinia virus containing a polynucleotide encoding IL-7 and vaccinia virus containing a polynucleotide encoding IL-12; or (2) vaccinia virus containing a polynucleotide encoding IL-7 and a polynucleotide encoding IL-12, and to be used in combination with an immune checkpoint inhibitor.

In an embodiment, the combined medicine of the present invention is a combined medicine for use in treating cancer, containing a pharmaceutical composition containing vaccinia virus containing a polynucleotide encoding IL-7 and a pharmaceutical composition containing vaccinia virus containing a polynucleotide encoding IL-12, and to be used in combination with an immune checkpoint inhibitor.

In an embodiment, the combined medicine of the present invention is a combined medicine for use in treating cancer, containing the pharmaceutical composition of the present invention containing the vaccinia virus to be used in the present invention or the combined medicine of the present invention and a pharmaceutical composition containing an immune checkpoint inhibitor.

In an embodiment, the pharmaceutical composition of the present invention is a pharmaceutical composition for use in treating cancer, containing an immune checkpoint inhibitor and to be used in combination with the pharmaceutical composition of the present invention containing the vaccinia virus to be used in the present invention or the combined medicine of the present invention.

In the pharmaceutical composition and combined medicine of the present invention, if the subject is a human, human IL-7 and human IL-12 can be used as IL-7 and IL-12, respectively. If the subject is a human and an antibody is used as the immune checkpoint inhibitor, the antibody is preferably an antibody against a human protein and can be a human chimeric antibody, a humanized antibody or a human antibody. The combined medicine of the present invention may be supplied as a kit (also referred to as "a combination kit") consisting of a single package containing components, i.e., pharmaceutical compositions.

The pharmaceutical composition or combined medicine of the present invention may further contain a pharmaceutically acceptable excipient.

The pharmaceutical composition of the present invention can be prepared by using an excipient ordinarily used in the art, i.e., a pharmaceutically acceptable excipient and a pharmaceutically acceptable carrier in accordance with a method ordinarily used. The dosage form of the pharmaceutical composition may include, for example, a parenteral agent such as an injection and a drip agent, which can be administered intravenously, subcutaneously or intratumorally. In preparing a drug product, e.g., an excipient, a carrier or additives can be used in accordance with the dosage form and within a pharmaceutically acceptable range. The pharmaceutical composition and combination kit of the present invention each may be provided as a lyophilized preparation. The lyophilized preparation can be provided together with water for injection.

The effective dose of the vaccinia virus to be used in the present invention varies depending on the degree of symptom and age of the patient, dosage form of the preparation to be used or titer of the virus; for example, as the effective dose of a single virus, more specifically, a total effective dose of two types of viruses contained in a combination kit, or a total effective dose of two types of viruses to be administered in combination, a plaque formation unit (PFU) of about $10^2$ to $10^{10}$ can be used.

The ratio of the dosages of two types of viruses that can be used in a combination kit is, for example, about 1:10 to 10:1, about 1:5 to 5:1, about 1:3 to 3:1, about 1:2 to 2:1, or about 1:1.

Application to Cancer Prevention or Therapy

The pharmaceutical composition and combined medicine of the present invention can be used for treating cancer, for example, solid cancer, for example but not limited to, a cancer selected from the group consisting of malignant melanoma, lung cancer, lung adenocarcinoma, small cell lung cancer, lung squamous cell carcinoma, kidney cancer, bladder cancer, head and neck cancer, breast cancer, esophagus cancer, glioblastoma, neuroblastoma, myeloma, ovarian cancer, colorectal cancer, pancreatic cancer, prostate cancer, hepatocellular carcinoma, mesothelioma, cervical cancer and stomach cancer.

The present invention provides a method for treating cancer in a subject (for example, patient) in need thereof, comprising administering a pharmaceutical composition containing the vaccinia virus to be used in the present invention and an immune checkpoint inhibitor to the subject, wherein the cancer is, for example, solid cancer, for example but not limited to, a cancer selected from the group consisting of malignant melanoma, lung cancer, lung adenocarcinoma, small cell lung cancer, lung squamous cell carcinoma, kidney cancer, bladder cancer, head and neck cancer, breast cancer, esophagus cancer, glioblastoma, neuroblastoma, myeloma, ovarian cancer, colorectal cancer, pancreatic cancer, prostate cancer, hepatocellular carcinoma, mesothelioma, cervical cancer and stomach cancer.

In an embodiment, the present invention provides a method for treating cancer in a subject (for example, patient) in need thereof, comprising administering the following (1), (2) and (3) to the subject, wherein the cancer is, for example, solid cancer, for example but not limited to, a cancer selected from the group consisting of malignant melanoma, lung cancer, lung adenocarcinoma, small cell lung cancer, lung squamous cell carcinoma, kidney cancer, bladder cancer, head and neck cancer, breast cancer, esophagus cancer, glioblastoma, neuroblastoma, myeloma, ovarian cancer, colorectal cancer, pancreatic cancer, prostate cancer, hepatocellular carcinoma, mesothelioma, cervical cancer and stomach cancer, (1) vaccinia virus containing a polynucleotide encoding IL-7;
(2) vaccinia virus containing a polynucleotide encoding IL-12; and
(3) an immune checkpoint inhibitor.

The vaccinia viruses (1) and (2) and the immune checkpoint inhibitor (3) may be administered to a subject in combination or separately. When the vaccinia viruses (1) and (2) and the immune checkpoint inhibitor (3) are administered separately, they may be simultaneously or sequentially administered. When the vaccinia viruses (1) and (2) and the immune checkpoint inhibitor (3) are sequentially administered, they may be administered continuously or at a time interval. In an embodiment, vaccinia viruses are administered, and then, the immune checkpoint inhibitor is administered. The vaccinia viruses can be administered, e.g., intratumorally, intravenously or intraperitoneally. The immune checkpoint inhibitor can be administered intratumorally, intravenously or intraperitoneally.

In an embodiment, the present invention provides a method for treating cancer in a subject (for example, patient) in need thereof, comprising administering the following (1) and (2) to the subject, wherein the cancer is, for example, solid cancer, for example but not limited to, a cancer selected from the group consisting of malignant melanoma, lung cancer, lung adenocarcinoma, small cell lung cancer, lung squamous cell carcinoma, kidney cancer, bladder cancer, head and neck cancer, breast cancer, esophagus cancer, glioblastoma, neuroblastoma, myeloma, ovarian cancer, colorectal cancer, pancreatic cancer, prostate cancer, hepatocellular carcinoma, mesothelioma, cervical cancer and stomach cancer,
(1) vaccinia virus containing a polynucleotide encoding IL-7 and a polynucleotide encoding IL-12; and
(2) an immune checkpoint inhibitor.

The vaccinia virus (1) and the immune checkpoint inhibitor (2) may be administered to a subject in combination or separately. When the vaccinia virus (1) and the immune checkpoint inhibitor (2) are administered separately, they may be simultaneously or sequentially administered. When the vaccinia virus (1) and the immune checkpoint inhibitor (2) are sequentially administered, they may be continuously administered or at a time interval. In an embodiment, vaccinia virus is administered, and then, the immune checkpoint inhibitor is administered.

The present invention provides the vaccinia virus and/or immune checkpoint inhibitor to be used in the present invention for use in treating cancer, for example, solid cancer, for example but not limited to, a cancer selected from the group consisting of malignant melanoma, lung cancer, lung adenocarcinoma, small cell lung cancer, lung squamous cell carcinoma, kidney cancer, bladder cancer, head and neck cancer, breast cancer, esophagus cancer, glioblastoma, neuroblastoma, myeloma, ovarian cancer, colorectal cancer, pancreatic cancer, prostate cancer, hepatocellular carcinoma, mesothelioma, cervical cancer and stomach cancer.

In an embodiment, the present invention provides vaccinia virus selected from the following (1) to (4), for use in treating cancer, for example, solid cancer, for example but not limited to, a cancer selected from the group consisting of malignant melanoma, lung cancer, lung adenocarcinoma, small cell lung cancer, lung squamous cell carcinoma, kidney cancer, bladder cancer, head and neck cancer, breast cancer, esophagus cancer, glioblastoma, neuroblastoma, myeloma, ovarian cancer, colorectal cancer, pancreatic cancer, prostate cancer, hepatocellular carcinoma, mesothelioma, cervical cancer and stomach cancer.

(1) vaccinia virus containing a polynucleotide encoding IL-7, to be used in combination with vaccinia virus containing a polynucleotide encoding IL-12 and an immune checkpoint inhibitor;
(2) vaccinia virus containing a polynucleotide encoding IL-12, to be used in combination with vaccinia virus containing a polynucleotide encoding IL-7 and an immune checkpoint inhibitor;
(3) vaccinia virus containing a polynucleotide encoding IL-7 and a polynucleotide encoding IL-12, to be used in combination with an immune checkpoint inhibitor; and
(4) a combination of vaccinia virus containing a polynucleotide encoding IL-7 and vaccinia virus containing a polynucleotide encoding IL-12, to be used in combination with an immune checkpoint inhibitor.

In an embodiment, the present invention provides an immune checkpoint inhibitor, for use in treating cancer, for example, solid cancer, for example but not limited to, a cancer selected from the group consisting of malignant melanoma, lung cancer, lung adenocarcinoma, small cell lung cancer, lung squamous cell carcinoma, kidney cancer, bladder cancer, head and neck cancer, breast cancer, esophagus cancer, glioblastoma, neuroblastoma, myeloma, ovarian cancer, colorectal cancer, pancreatic cancer, prostate cancer, hepatocellular carcinoma, mesothelioma, cervical cancer and stomach cancer, and
to be used in combination with
(1) vaccinia virus containing a polynucleotide encoding IL-7 and vaccinia virus containing a polynucleotide encoding IL-12; or
(2) vaccinia virus containing a polynucleotide encoding IL-7 and a polynucleotide encoding IL-12.

The present invention further provides use of vaccinia virus selected from the following (1) to (4), for the manufacture of the pharmaceutical composition or combined medicine of the present invention for use in treating cancer, for example, solid cancer, for example but not limited to, a cancer selected from the group consisting of malignant melanoma, lung cancer, lung adenocarcinoma, small cell lung cancer, lung squamous cell carcinoma, kidney cancer, bladder cancer, head and neck cancer, breast cancer, esophagus cancer, glioblastoma, neuroblastoma, myeloma, ovarian cancer, colorectal cancer, pancreatic cancer, prostate cancer, hepatocellular carcinoma, mesothelioma, cervical cancer and stomach cancer,
(1) vaccinia virus containing a polynucleotide encoding IL-7, to be used in combination with vaccinia virus containing a polynucleotide encoding IL-12 and an immune checkpoint inhibitor;
(2) vaccinia virus containing a polynucleotide encoding IL-12, to be used in combination with vaccinia virus containing a polynucleotide encoding IL-7 and an immune checkpoint inhibitor;
(3) vaccinia virus containing a polynucleotide encoding IL-7 and a polynucleotide encoding IL-12, to be used in combination with an immune checkpoint inhibitor; and
(4) a combination of vaccinia virus containing a polynucleotide encoding IL-7 and vaccinia virus containing a polynucleotide encoding IL-12, to be used in combination with an immune checkpoint inhibitor.

The present invention further provides use of an immune checkpoint inhibitor for the manufacture of the pharmaceutical composition or combined medicine of the present invention for use in treating cancer, for example, solid cancer, for example but not limited to, a cancer selected from the group consisting of malignant melanoma, lung cancer, lung adenocarcinoma, small cell lung cancer, lung squamous cell carcinoma, kidney cancer, bladder cancer, head and neck cancer, breast cancer, esophagus cancer, glioblastoma, neuroblastoma, myeloma, ovarian cancer, colorectal cancer, pancreatic cancer, prostate cancer, hepatocellular carcinoma, mesothelioma, cervical cancer and stomach cancer, in which the pharmaceutical composition or combined medicine (1) is to be used in combination with vaccinia virus containing a polynucleotide encoding IL-7 and vaccinia virus containing a polynucleotide encoding IL-12;

(2) is to be used in combination with vaccinia virus containing a polynucleotide encoding IL-7 and a polynucleotide encoding IL-12;

(3) contains vaccinia virus containing a polynucleotide encoding IL-7, and is to be used in combination with vaccinia virus containing a polynucleotide encoding IL-12; or (4) contains vaccinia virus containing a polynucleotide encoding IL-12, and is to be used in combination with vaccinia virus containing a polynucleotide encoding IL-7.

The present invention further provides use of at least one or all selected from the group consisting of vaccinia virus containing a polynucleotide encoding IL-7 and a polynucleotide encoding IL-12 and an immune checkpoint, in the manufacture of a combined medicine for use in treating cancer, for example, solid cancer, for example but not limited to, a cancer selected from the group consisting of malignant melanoma, lung cancer, lung adenocarcinoma, small cell lung cancer, lung squamous cell carcinoma, kidney cancer, bladder cancer, head and neck cancer, breast cancer, esophagus cancer, glioblastoma, neuroblastoma, myeloma, ovarian cancer, colorectal cancer, pancreatic cancer, prostate cancer, hepatocellular carcinoma, mesothelioma, cervical cancer and stomach cancer, containing a pharmaceutical composition containing vaccinia virus containing a polynucleotide encoding IL-7 and a polynucleotide encoding IL-12, and a pharmaceutical composition containing an immune checkpoint inhibitor.

The present invention further provides use of at least one or all selected from the group consisting of vaccinia virus containing a polynucleotide encoding IL-7 and vaccinia virus containing a polynucleotide encoding IL-12 and an immune checkpoint inhibitor, for the manufacture of a combined medicine for use in treating cancer, for example, solid cancer, for example but not limited to, a cancer selected from the group consisting of malignant melanoma, lung cancer, lung adenocarcinoma, small cell lung cancer, lung squamous cell carcinoma, kidney cancer, bladder cancer, head and neck cancer, breast cancer, esophagus cancer, glioblastoma, neuroblastoma, myeloma, ovarian cancer, colorectal cancer, pancreatic cancer, prostate cancer, hepatocellular carcinoma, mesothelioma, cervical cancer and stomach cancer, containing a pharmaceutical composition containing vaccinia virus containing a polynucleotide encoding IL-7, a pharmaceutical composition containing vaccinia virus containing a polynucleotide encoding IL-12 and a pharmaceutical composition containing an immune checkpoint inhibitor.

In the specification, the "for prevention" is used in the same sense as "for use in preventing" and the "for treatment" is used in the same sense as "for use in treating".

The pharmaceutical composition or combined medicine of the present invention can be used in combination with other various therapeutic agents having efficacy in cancer, for example, solid cancer, for example but not limited to, a cancer selected from the group consisting of malignant melanoma, lung cancer, lung adenocarcinoma, small cell lung cancer, lung squamous cell carcinoma, kidney cancer, bladder cancer, head and neck cancer, breast cancer, esophagus cancer, glioblastoma, neuroblastoma, myeloma, ovarian cancer, colorectal cancer, pancreatic cancer, prostate cancer, hepatocellular carcinoma, mesothelioma, cervical cancer and stomach cancer. The other various therapeutic agents may be non-immunotherapeutic drugs. The combination use may include simultaneous administration, separate and continuous administration, separate administration at a desired time interval. In the case of simultaneous administration, the pharmaceutical composition of the present invention may be a combined preparation or a combination of separate preparations.

In the cancer to be treated by the present invention, metastatic cancers to organs except an organ having a primary lesion, such as lymph node and liver, are included. Accordingly, in the present invention, a subject having a metastatic cancer is also included in the subject.

Administration Order of Vaccinia Virus and Immune Checkpoint Inhibitor

In the present invention, vaccinia virus and an immune checkpoint inhibitor can be administered simultaneously or continuously or sequentially.

In an embodiment, administration of vaccinia virus to a subject having cancer is started, and thereafter, administration of an immune checkpoint inhibitor is started. In an embodiment, administration of an immune checkpoint inhibitor to a subject having cancer is started, and thereafter, administration of vaccinia virus is started.

In an embodiment, administration of vaccinia virus to a subject having cancer is completed, and thereafter, administration of an immune checkpoint inhibitor is started. In an embodiment, administration of an immune checkpoint inhibitor to a subject having cancer is completed, and thereafter, administration of vaccinia virus is started.

In an embodiment, vaccinia virus and immune checkpoint inhibitor can be administered to a subject having cancer in accordance with dosing schedule including a dosing cycle. In an embodiment, in at least one dosing cycle or all dosing cycles, administration of vaccinia virus to a subject having cancer is started, and thereafter, administration of an immune checkpoint inhibitor can be started. In an embodiment, in at least one dosing cycle or all dosing cycles, administration of vaccinia virus to a subject having cancer is completed, and thereafter, administration of an immune checkpoint inhibitor can be started. In an embodiment, in at least one dosing cycle or all dosing cycles, administration of an immune checkpoint inhibitor to a subject having cancer is started, and thereafter, administration of vaccinia virus can be started. In an embodiment, in at least one dosing cycle or all dosing cycles, administration of an immune checkpoint inhibitor to a subject having cancer is completed, and thereafter, administration of vaccinia virus can be started.

In the present invention, if vaccinia virus containing a polynucleotide encoding IL-7 and vaccinia virus containing a polynucleotide encoding IL-12 are different, the vaccinia viruses may be simultaneously, continuously or sequentially administered. Also, in this embodiment, the administration order of vaccinia virus and an immune checkpoint inhibitor can be determined in accordance with the administration order as mentioned above.

The present invention has been generally described. In order to further obtain understanding of the invention, Examples will be described for reference; however, these are provided just for the purpose of illustration and do not limit the present invention.

EXAMPLES

Example 1: Antitumor Effect on Tumor-Bearing Mouse by Combination Use of Genetically Modified Vaccinia Virus and Another Cancer Therapy As a genetically modified vaccinia virus, vaccinia virus (LC16mO ΔSCR VGF-SP-IL12/O1L-SP-IL7) containing polynucleotides encoding IL-12 (IL12) and IL-7 (IL7) (hereinafter referred to as "IL12 and IL7 integrated vaccinia virus") described in WO2017/209053 (Example 2) such that the polynucleotides can be expressed was selected and put in use. As the cancer therapy, a cancer immunotherapy, particularly, a cancer immunotherapy using an immune checkpoint inhibitor was selected and used in combination with vaccinia virus mentioned above. As the immune checkpoint inhibitor, an anti-mouse PD-1 antibody and anti-mouse CTLA-4 antibody were used.

Complete remission induction effect by combination use with the anti-PD-1 antibody or anti-CTLA-4 antibody was evaluated by using mice (tumor-bearing mice) having a syngenic-mouse cancer cell strain subcutaneously transplanted in each of the left and right lateral region of the abdomen.

More specifically, first, to each of the left and right lateral region of the abdomen of BALB/c mice (male, 5-6 weeks old, Charles River Laboratories Japan, Inc.), 50 µL of mouse colon cancer cells CT26.WT (ATCC CRL-2638) prepared by PBS to be $1 \times 10^7$ cells/mL was subcutaneously transplanted. Day 7 after the subcutaneous transplantation of cancer cells, the diameter of tumors was measured by a caliper. The mice were classified into the following 6 groups such that an average tumor volume (minor diameter mm×minor diameter mm×major diameter mm×0.52) satisfies 24 to 29 mm$^3$ at the virus administration side (right lateral region of abdomen) and 24 to 26 mm$^3$ at the non-virus administration side (left lateral region of abdomen: remote tumor).

Administration group:
1) solvent administration group;
2) single-agent administration group with an anti-PD-1 antibody;
3) single-agent administration group with an anti-CTLA-4 antibody;
4) single-agent administration group with IL12 and IL7-carrying vaccinia virus;
5) combination administration group with IL12 and IL7-carrying vaccinia virus and an anti-PD-1 antibody; and
6) combination administration group with IL12 and IL7-carrying vaccinia virus and an anti-CTLA-4 antibody.

In the solvent administration group, 30 µL of a solvent (30 mM Tris-HCl, 10% sucrose) was injected within a tumor in the mouse right lateral region of the abdomen, Day 1, Day 3 and Day 6 after grouping. In the single-agent administration group with IL12 and IL7-carrying vaccinia virus, the combination administration group with IL12 and IL7-carrying vaccinia virus and an anti-PD-1 antibody and the combination administration group with IL12 and IL7-carrying vaccinia virus and an anti-CTLA-4 antibody, 30 µL of IL12 and IL7-carrying vaccinia virus diluted with a solvent up to a concentration of $6.7 \times 10^8$ PFU/mL was injected ($2 \times 10^7$ PFU) in a tumor in the mouse right lateral region of the abdomen, Day 1, Day 3 and Day 6 after grouping.

In the single-agent administration group with an anti-PD-1 antibody, the single-agent administration group with an anti-CTLA-4 antibody, the combination administration group with IL12 and IL7-carrying vaccinia virus and an anti-PD-1 antibody and the combination administration group with IL12 and IL7-carrying vaccinia virus and an anti-CTLA-4 antibody, an anti-PD-1 antibody (RMP1-14) (BE0146, Bio X Cell) diluted with PBS up to a concentration of 1 mg/mL or an anti-CTLA-4 antibody (9D9) (BE0164, Bio X Cell) diluted with PBS up to a concentration of 2 mg/mL was intraperitoneally injected in an amount of 100 µL, on and after Day 6 after grouping, twice a week. The anti-PD-1 antibody (RMP1-14) can neutralize the binding between PD-1 and PD-L1, and PD-1 and PD-L2, and can brock signal transduction through PD-1. Also, anti-CTLA-4 antibody (9D9) can block signal transduction through CTLA-4. In the solvent administration group and the single-agent administration group of IL12 and IL7-carrying vaccinia virus, 100 µL of PBS was intraperitoneally administered twice a week on and after Day 6 after grouping. The diameter of the tumors present in left and right lateral regions of the abdomen was measured by a caliper, twice a week to calculate the tumor volumes. The case where no tumor is observed by palpation at the final observation carried out Day 37 after grouping, was determined as complete remission (CR) and the number of individuals attained complete remission was counted.

As a result, as shown in the upper panels of FIG. 1, with respect to tumors in the right lateral region of the abdomen (virus administration side), complete remission was achieved in 9 out of 10 cases in the single-agent administration group with IL12 and IL7-carrying vaccinia virus; 10 out of 10 cases in the combination administration group with IL12 and IL7-carrying vaccinia virus and an anti-PD-1 antibody; and 9 out of 10 cases in the combination administration group with IL12 and IL7-carrying vaccinia virus and an anti-CTLA-4 antibody. Antitumor action was not apparently observed in the single-agent administration group with an anti-PD-1 antibody and the single-agent administration group with an anti-CTLA-4 antibody, compared to the solvent administration group.

In contrast, as shown in the lower panels of FIG. 1, with respect to tumors in the left lateral region of the abdomen (non-virus administration side), complete remission was achieved in only one out of 10 cases in the single-agent administration group with IL12 and IL7-carrying vaccinia virus; 6 out of 10 cases in the combination administration group with IL12 and IL7-carrying vaccinia virus and an anti-PD-1 antibody; and 4 out of 10 cases in the combination administration group with IL12 and IL7-carrying vaccinia virus and an anti-CTLA-4 antibody.

From the results, it was found, in a tumor-bearing mouse model, that the combination administration with IL12 and IL7-carrying vaccinia virus and an anti-PD-1 antibody, and the combination administration with IL12 and IL7-carrying vaccinia virus and an anti-CTLA-4 antibody have an excellent antitumor effect compared to the single-agent administration with an anti-PD-1 antibody, and single-agent administration with an anti-CTLA-4 antibody; and have a high complete remission induction effect also on a tumor (remote tumor) away from the administration site with vaccinia virus compared to the single-agent administration with an anti-PD-1 antibody, single-agent administration with an anti-CTLA-4 antibody, and single-agent administration with IL12 and IL7-carrying vaccinia virus.

INDUSTRIAL APPLICABILITY

The cancer therapy by combination of vaccinia virus with an immune checkpoint inhibitor employed in the present invention and a pharmaceutical composition and a combined medicine to be used for the therapy are expected to be useful for preventing or treating various cancers.

What is claimed is:

1. A method of treating cancer, comprising administering
(i) a pharmaceutical composition comprising
   (1) a vaccinia virus comprising a polynucleotide encoding interleukin-7 (IL-7) and a vaccinia virus comprising a polynucleotide encoding interleukin-12 (IL-12); or
   (2) a vaccinia virus comprising a polynucleotide encoding IL-7 and a polynucleotide encoding IL-12, wherein the vaccinia viruses are LC16mO strain and are defective in functions of vaccinia virus growth factor (VGF) and O1L and lack an SCR (short consensus repeat) domain in a B5R extracellular region; and
(ii) an immune checkpoint inhibitor
to a subject with cancer, wherein the vaccinia viruses are intratumorally administered.

2. The method according to claim 1, wherein the pharmaceutical composition comprises the vaccinia virus comprising the polynucleotide encoding IL-7 and the polynucleotide encoding IL-12.

3. The method according to claim 1, wherein the immune checkpoint inhibitor is an antibody selected from the group consisting of an anti-PD-1 antibody, an anti-PD-L1 antibody and an anti-CTLA-4 antibody, or an antigen-binding fragment thereof.

4. The method according to claim 1, wherein the cancer is solid cancer.

5. The method according to claim 1, wherein the cancer is metastatic cancer.

6. The method according to claim 1, wherein the pharmaceutical composition and the immune checkpoint inhibitor are administered concurrently.

7. The method according to claim 1, wherein the immune checkpoint inhibitor is administered before or after the pharmaceutical composition.

8. The method of claim 1, wherein the pharmaceutical composition comprises the vaccinia virus comprising the polynucleotide encoding IL-7 and the vaccinia virus comprising a polynucleotide encoding IL-12.

* * * * *